United States Patent
Hirayama et al.

(10) Patent No.: US 8,350,802 B2
(45) Date of Patent: Jan. 8, 2013

(54) ELECTROPHORETIC DEVICE WITH CAPACITIVE STORAGE AND APPLIED FLUCTUATING SIGNAL, METHOD OF DRIVING THE SAME, AND ELECTRONIC APPARATUS

(75) Inventors: Hiroshi Hirayama, Shiojiri (JP); Junpei Yoshida, Tino (JP)

(73) Assignee: Seiko Epson Corporation (JP)

( * ) Notice: Subject to any disclaimer, the term of this patent is extended or adjusted under 35 U.S.C. 154(b) by 776 days.

(21) Appl. No.: 12/019,342

(22) Filed: Jan. 24, 2008

(65) Prior Publication Data
US 2008/0277279 A1 Nov. 13, 2008

(30) Foreign Application Priority Data
Jan. 25, 2007 (JP) .................. 2007-015104

(51) Int. Cl.
*G09G 3/34* (2006.01)
(52) U.S. Cl. .................................................. 345/107
(58) Field of Classification Search .................. 345/107
See application file for complete search history.

(56) References Cited

U.S. PATENT DOCUMENTS

| | | | | |
|---|---|---|---|---|
| 5,345,251 A * | 9/1994 | DiSanto et al. | ............... | 345/107 |
| 5,392,058 A * | 2/1995 | Tagawa | .................. | 345/104 |
| 6,724,521 B2 * | 4/2004 | Nakao et al. | ................. | 359/296 |
| 2001/0030639 A1 * | 10/2001 | Goden | ............... | 345/107 |
| 2004/0145696 A1 * | 7/2004 | Oue et al. | ................ | 349/167 |
| 2004/0263701 A1 * | 12/2004 | Ukigaya | .................. | 349/36 |
| 2005/0146775 A1 * | 7/2005 | Chung et al. | ................. | 359/296 |
| 2006/0209011 A1 * | 9/2006 | Miyasaka | ............... | 345/107 |
| 2007/0002008 A1 * | 1/2007 | Tam | ............... | 345/107 |
| 2007/0008278 A1 * | 1/2007 | Johnson et al. | ............... | 345/107 |

FOREIGN PATENT DOCUMENTS
JP 2002-149115 5/2002

* cited by examiner

*Primary Examiner* — Chanh Nguyen
*Assistant Examiner* — Sanghyuk Park
(74) *Attorney, Agent, or Firm* — Harness, Dickey & Pierce, P.L.C.

(57) ABSTRACT

Disclosed is a method of driving an electrophoretic device that includes an electrophoretic element having a first electrode, a second electrode, and an electrophoretic layer disposed between the first and second electrodes, and further includes a capacitor connected to the first electrode at one terminal. The method includes (a) applying a reference potential or a first potential higher than the reference potential to the first electrode of the electrophoretic element and the terminal of the capacitor and applying the reference potential to the second electrode of the electrophoretic element, and (b) applying a signal fluctuating between a second potential and a third potential to the second electrode subsequently to the step (a), the second potential being equal to or higher than the reference potential, the third potential being higher than the second potential and being equal to or lower than the first potential.

10 Claims, 8 Drawing Sheets

ELECTROPHORETIC DEVICE WITH CAPACITIVE STORAGE AND APPLIED FLUCTUATING SIGNAL, METHOD OF DRIVING THE SAME, AND ELECTRONIC APPARATUS

BACKGROUND

1. Technical Field

The present invention relates to a technique for driving an electrophoretic device.

2. Related Art

JP-A-2002-149115 discloses a related art of an active matrix electrophoretic device. According to this related art, an electrophoretic device drives pixels using a driving method called a two-step writing method by means of pixel circuits each including a single transistor and a single capacitor (i.e., 1T1C pixel circuits). According to the two-step writing method, a voltage for white display (or black display) is written into each pixel (in order to erase the display of each pixel) and, after that, a voltage for white display (or a voltage for black display) is appropriately written into the pixels in accordance with display data, thus forming an image, such as a picture or characters. As for erase operations, writing a voltage for white display into each pixel is called "whole white erasure" and writing a voltage for black display into each pixel is called "whole black erasure.

In typical electrophoretic devices utilizing the above-described whole white erasure or whole black erasure, however, each erase operation requires approximately one second. It is disadvantageous in terms of a reduction in image rewrite time. When the whole white erasure and whole black erasure are used in combination in order to prevent image lag, the combined erase operation requires two or more seconds. It is more disadvantageous. One of related-art approaches whereby the above-described disadvantages can be avoided is a simultaneous writing method using the above-described 1T1C pixel circuits. The simultaneous writing method has no erase operation before writing a voltage into each pixel. There is no problem from the viewpoint of the image rewrite time. However, this method requires a power source providing a large potential difference. Disadvantageously, it results in an increase in power consumption of the electrophoretic device. This disadvantage is significant because the electrophoretic device offers or is expected to offer an advantage in that the power consumption is low. According to another related art, an electrophoretic device includes a latch circuit that is incorporated into each pixel circuit. The latch type electrophoretic device needs many (for example, five) transistors in each pixel circuit. Disadvantageously, this arrangement may easily cause a reduction in yield.

SUMMARY

An advantage of some aspects of the invention is to provide an electrophoretic device capable of solving the above-described disadvantages and reducing rewrite time and a method of driving the electrophoretic device.

According to an aspect of the invention, there is provided a method of driving an electrophoretic device that includes an electrophoretic element having a first electrode, a second electrode, and an electrophoretic layer disposed between the first and second electrodes, and further includes a capacitor connected to the first electrode at one terminal. The method includes (a) applying a reference potential or a first potential higher than the reference potential to the first electrode of the electrophoretic element and the terminal of the capacitor and applying the reference potential to the second electrode of the electrophoretic element, and (b) applying a signal fluctuating between a second potential and a third potential to the second electrode subsequently to the step (a), the second potential being equal to or higher than the reference potential, the third potential being higher than the second potential and being equal to or lower than the first potential.

According to another aspect of the invention, there is provided a method of driving an electrophoretic device having a plurality of pixels arranged in a matrix of m rows and n columns, each pixel including an electrophoretic element that includes a first electrode, a second electrode, and an electrophoretic layer disposed between the first and second electrodes, each pixel further including a capacitor connected to the first electrode at one terminal. The method includes (a) sequentially selecting the pixels in the respective rows, applying a reference potential or a first potential higher than the reference potential to the first electrode of the electrophoretic element and the terminal of the capacitor in each selected pixel, and applying the reference potential to the second electrode of the electrophoretic element, and (b) applying a signal fluctuating between a second potential and a third potential to the second electrode subsequently to the step (a), the second potential being equal to or higher than the reference potential, the third potential being higher than the second potential and being equal to or lower than the first potential.

As described above, in the related-art two-step writing method, the erase operation is performed prior to writing a voltage into an electrophoretic element (hereinafter, referred to as "voltage write operation"). Accordingly, it takes long time for rewriting. In each of the methods according to the above-described aspects of the invention, in the step (a), while the first potential is applied to the first electrode of the photoelectric element and the reference potential is applied to the second electrode thereof (a first state), alternatively, while the reference potential is applied to each of the first and second electrodes (a second state), a voltage is written into the electrophoretic element. Accordingly, a state of the electrophoretic element can be rewritten more rapidly than the case where the erase operation is performed before the voltage write operation. In addition, since the potential written in the first electrode is held by the capacitor for a certain period, control for the next step (b) can be performed for this period. In other words, the potential applied to the second electrode is allowed to fluctuate between the second potential and the third potential. Consequently, for example, in the above-described first state, the potential of the first electrode is periodically made higher than that of the second electrode, thus accelerating migration of electrophoretic particles. Similarly, in the above-described second state, the potential of the second electrode is periodically made higher than that of the first electrode, thus accelerating migration of electrophoretic particles. Advantageously, in each of the first and second states, if the voltage write operation in the step (a) is insufficiently performed, an effect of complementing the insufficient operation can be obtained. In other words, in each of the methods according to the aspects of the invention, electrophoretic particles in the electrophoretic element can be more reliably dispersed in a desired state irrespective of a voltage write state (the first or second state) in the step (a) by application of a fluctuating signal in the step (b). Thus, for example, an image can be sharpened.

In each of the methods, preferably, the second potential is equal to the reference potential and the third potential is equal to the first potential.

Consequently, the kinds of potentials to be generated in the electrophoretic device is small in number, so that potential control can be more easily made. The structure of a mechanism for potential generation can be simplified.

In each of the methods, it is preferable that the second potential be higher than the reference potential and the third potential be lower than the first potential.

Consequently, if a so-called kickback phenomenon remarkably occurs, the voltage write operation can be efficiently performed.

In each of the methods, preferably, the steps (a) and (b) are repeated a plurality of times.

Advantageously, a hold capacitance necessary for the capacitor can be reduced.

According to another aspect of the invention, an electrophoretic device includes the following elements. An electrophoretic element includes a first electrode, a second electrode, and an electrophoretic layer disposed between the first and second electrodes. A capacitor is connected to the first electrode at one terminal. A drive circuit is connected to the electrophoretic element and the capacitor. The drive circuit performs (a) applying a reference potential or a first potential higher than the reference potential to the first electrode of the electrophoretic element and the terminal of the capacitor and applying the reference potential to the second electrode of the electrophoretic element, and (b) applying a signal fluctuating between a second potential and a third potential to the second electrode subsequently to the step (a), the second potential being equal to or higher than the reference potential, the third potential being higher than the second potential and being equal to or lower than the first potential.

According to another aspect of the invention, an electrophoretic device includes a plurality of pixels arranged in a matrix of m rows and n columns, and a drive circuit connected to the pixels. Each pixel includes the following elements. An electrophoretic element includes a first electrode, a second electrode, and an electrophoretic layer disposed between the first and second electrodes. A capacitor is connected to the first electrode at one terminal. The drive circuit performs (a) sequentially selecting the pixels in the respective rows, applying a reference potential or a first potential higher than the reference potential to the first electrode of the electrophoretic element and the terminal of the capacitor in each selected pixel, and applying the reference potential to the second electrode of the electrophoretic element, and (b) applying a signal fluctuating between a second potential and a third potential to the second electrode subsequently to the step (a), the second potential being equal to or higher than the reference potential, the third potential being higher than the second potential and being equal to or lower than the first potential.

As described above, in the related-art two-step writing method, the erase operation is performed prior to the voltage write operation on an electrophoretic element. Accordingly, it takes long time for rewriting. In each of the electrophoretic devices according to the above-described aspects of the invention, in the step (a), while the first potential is applied to the first electrode of the photoelectric element and the reference potential is applied to the second electrode thereof (a first state), alternatively, while the reference potential is applied to each of the first and second electrodes (a second state), the drive circuit writes a voltage into the electrophoretic element. Accordingly, a state of the electrophoretic element can be rewritten more rapidly than the case where the erase operation is performed before the voltage write operation. In addition, since the potential written in the first electrode is held by the capacitor for a certain period, the drive circuit can perform control for the next step (b) for this period. In other words, the potential applied to the second electrode is allowed to fluctuate between the second potential and the third potential. Consequently, for example, in the first state, the potential of the first electrode is periodically made higher than that of the second electrode, thus accelerating migration of electrophoretic particles. Similarly, in the second state, the potential of the second electrode is periodically made higher than that of the first electrode, thus accelerating migration of electrophoretic particles. Advantageously, in each of the first and second states, if the voltage write operation in the step (a) is insufficiently performed, an effect of complementing the insufficient operation can be obtained. In other words, in each of the electrophoretic devices according to the aspects of the invention, electrophoretic particles in the electrophoretic element can be more reliably dispersed in a desired state irrespective of a voltage write state (the first or second state) in the step (a) by application of a fluctuating signal in the step (b). Thus, for example, an image can be sharpened.

The second electrode may be a common electrode shared by the electrophoretic elements. Advantageously, the interconnection structure can be simplified.

In each of the above-described electrophoretic devices, preferably, the second potential is equal to the reference potential and the third potential is equal to the first potential.

Consequently, the kinds of potentials to be generated in the electrophoretic device is small in number, so that potential control can be more easily made. Thus, the structure of a mechanism for potential generation can be simplified.

In each of the electrophoretic devices, it is preferable that the second potential be higher than the reference potential and the third potential be lower than the first potential.

Consequently, if a so-called kickback phenomenon remarkably occurs, the voltage write operation can be efficiently performed.

In each of the electrophoretic devices, the drive circuit may repeat the steps (a) and (b) a plurality of times.

Consequently, a hold capacitance necessary for the capacitor can be reduced.

According to another aspect of the invention, an electronic apparatus includes any of the above-described electrophoretic devices as a display unit. In this instance, "electronic apparatuses" include various apparatuses, e.g., a display apparatus, a television apparatus, an electronic paper, a watch, an electronic calculator, a mobile phone, and a personal digital assistant, each including a display unit utilizing display by means of an electrophoretic layer. The "apparatuses" in the invention conceptually include, for example, flexible paper- and film-like objects, objects belonging to fixed properties, such as a wall surface with such a flexible object, and objects belonging to moving objects, such as a vehicle, an airplane, a boat, and a ship.

BRIEF DESCRIPTION OF THE DRAWINGS

The invention will be described with reference to the accompanying drawings, wherein like numbers reference like elements.

DESCRIPTION OF EXEMPLARY EMBODIMENTS

An embodiment of the invention will be described below with reference to the drawings.

Figure 1:
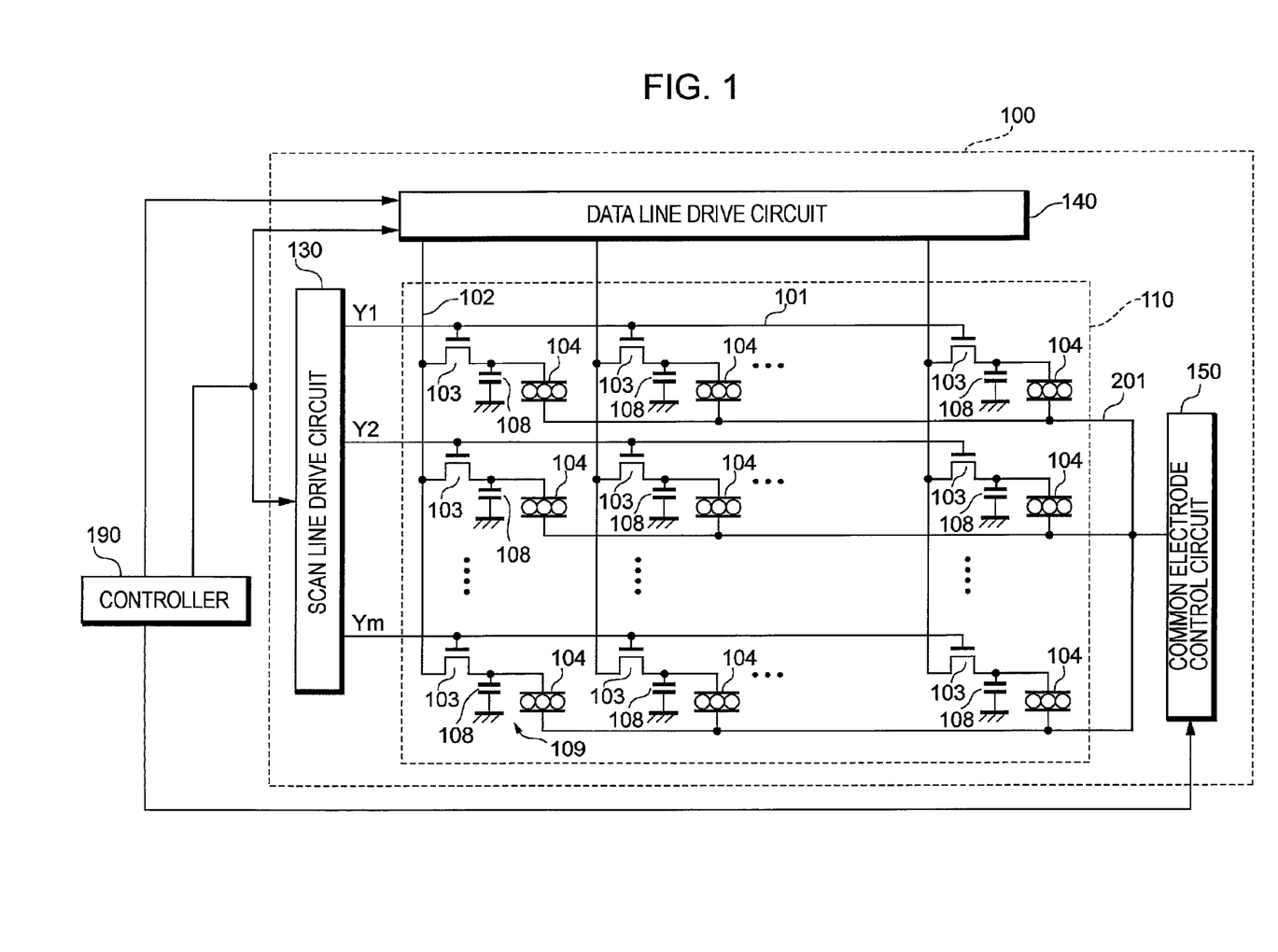
FIG. 1 is a block diagram illustrating the entire structure of an electrophoretic device.

FIG. 1 is a block diagram illustrating the entire structure of an electrophoretic device according to the present embodiment. Referring to FIG. 1, the electrophoretic device 100 includes a panel 110, a scan line drive circuit 130, a data line drive circuit 140, and a common electrode control circuit 150. The panel 110 includes m scan lines 101, n data lines 102 intersecting the scan lines 101, and pixels 109 arranged so as to correspond to the respective intersections of the scan lines 101 and the data lines 102. Each pixel 109 includes a transistor 103, an electrophoretic element 104, and a capacitor 108. The pixels 109 are arranged in a matrix.

Figure 2:
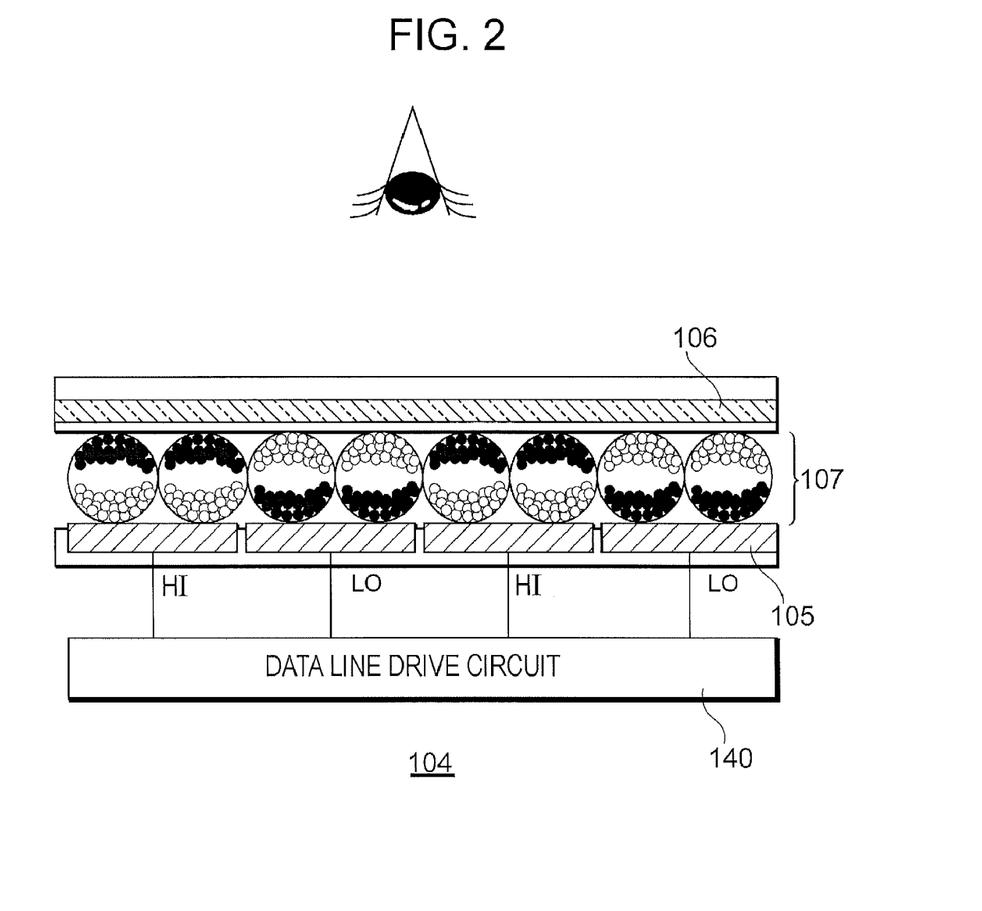
FIG. 2 is a diagram explaining the structure of electrophoretic element and includes a schematic cross-sectional view of the electrophoretic elements.

FIG. 2 is a diagram explaining the structure of the electrophoretic element 104 and includes a schematic cross sectional view of the electrophoresis elements 104. Each electrophoretic element 104 includes a first electrode 105, a second electrode 106, and an electrophoretic layer (electrophoretic material) 107 disposed between the first and second electrodes. In the embodiment, the first electrode 105 serves as a pixel electrode arranged for each individual pixel. The second electrode 106 serves as a common electrode shared by the respective pixels. The second electrode 106 receives a common electrode signal COM. The second electrode 106 may be separated into segments such that the segments correspond to the respective electrophoretic elements 104. In the embodiment, it is assumed that a state (i.e., display state) of the electrophoretic layer 107 is viewed from the side of the second electrode 106. The second electrode 106 includes a transparent conducting layer made of, for example, indium tin oxide (ITO).

The electrophoretic layer 107 includes many microcapsules containing positively charged black particles and negatively charged white particles. FIG. 2 schematically shows a state of the electrophoretic layer 107. In the embodiment, when the potential of the first electrode 105 is relatively higher than that of the second electrode 106 (this state is indicated by "HI" in FIG. 2), the positively charged black particles move toward the second electrode 106 and the negatively charged white particles move toward the first electrode 105. When a pixel in this state is viewed from the side of the second electrode 106, this pixel is recognized as black. On the other hand, when the potential of the first electrode 105 is relatively lower than that of the second electrode 106 (this state is indicated by "LO" in FIG. 2), the positively charged black particles move toward the first electrode 105 and the negatively charged white particles move toward the second electrode 106. When a pixel in this state is viewed from the side of the second electrode 106, this pixel is recognized as white. Although the electrophoretic device 100 according to the embodiment fundamentally provides two-level display of black and white, the device can also perform gray scale display using surrounding pixels in combination. The available structure of the electrophoretic layer 107 is not limited to the above-described microcapsule type. Furthermore, the colors applied to particles are not limited to black and white. The charged states of particles are not limited to the above-described pattern. In addition, the state of the electrophoretic layer 107 may be recognized from the side of either the first electrode 105 or the second electrode 106. In other words, the above-described conditions may be appropriately changed.

Figure 3:
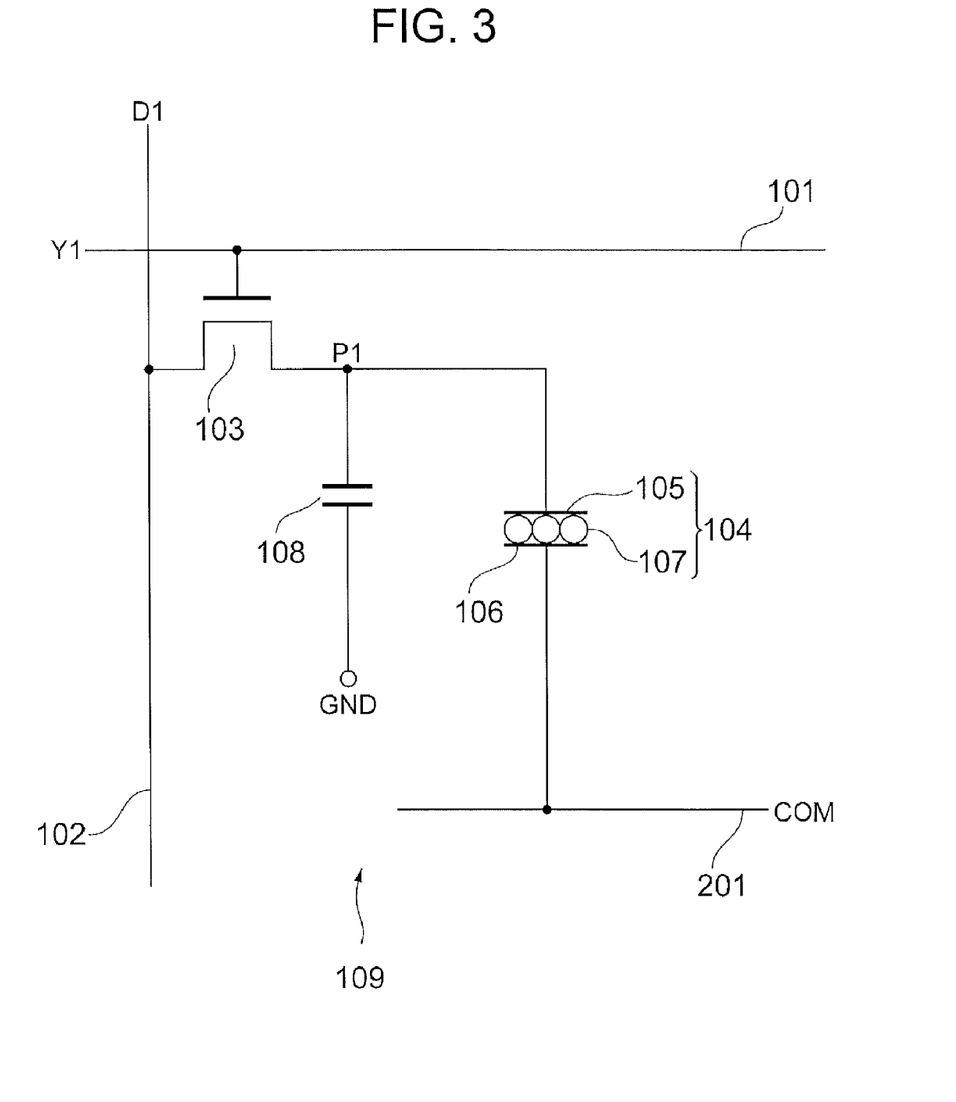
FIG. 3 is a circuit diagram showing the detailed structure of the pixel.

FIG. 3 is a circuit diagram illustrating the detailed structure of the pixel 109. The gate of the transistor 103, serving as a switching element, is connected to the scan line 101, the source thereof is connected to the data line 102, and the drain thereof is connected to the first electrode 105. The capacitor 108 is connected between the drain of the transistor 103 and a ground terminal (ground potential) GND. A scan signal Y1 is supplied to the scan line 101 in the first row. Scan signals Y2 to Ym are sequentially supplied to the scan lines 101 in the second to mth rows, respectively (refer to FIG. 4). A data signal D1 is supplied to the data line 102. The potential of the data signal D1 is held by the capacitor (hold capacitor) 108. The data signal D1 is supplied to the data line 102 in the first column. Data signals D2 to Dn are supplied to the data lines 102 in the second to nth columns, respectively. The electrophoretic element 104 includes the first electrode 105, the second electrode 106, and the electrophoretic layer 107 disposed between the first and second electrodes. The electrophoretic elements 104 are arranged in a matrix to constitute the panel 110. An electrostatic capacitance, whose magnitude depends on the electrode area of the first electrode 105, the distance between the first electrode 105 and the second electrode 106, and the dielectric constant of the electrophoretic layer 107, is generated between the first electrode 105 and the second electrode 106. The second electrode 106 is shared by the electrophoretic elements 104 and is connected to the common electrode control circuit 150 via interconnection lines 201 (see FIG. 1). A common electrode signal COM is supplied to each interconnection line 201. For example, either a reference potential that is relatively low (for example, 0 V) or a voltage at a relatively high potential (for example, +10 V) is applied as the common electrode signal COM.

The electrophoretic device 100 is connected to a controller 190, serving as a peripheral circuit. The controller 190 includes an image signal processing circuit and a timing generator. The image signal processing circuit generates image data and common electrode control data and supplies the image data and the control data to the data line drive circuit 140 and the common electrode control circuit 150, respectively. The common electrode control circuit 150 supplies the common electrode signal COM to the second electrode 106 of the electrophoretic element 104. When a reset operation is performed or the image signal processing circuit outputs image data, the timing generator generates various timing signals for control of the scan line drive circuit 130 and the data line drive circuit 140.

The above-described transistor 103, the scan line drive circuit 130, the data line drive circuit 140, and the common electrode control circuit 150 correspond to a "drive circuit" in the invention.

The structure of the electrophoretic device 100 according to the embodiment has been described above. The operation thereof will now be described in detail below.

Figure 4:
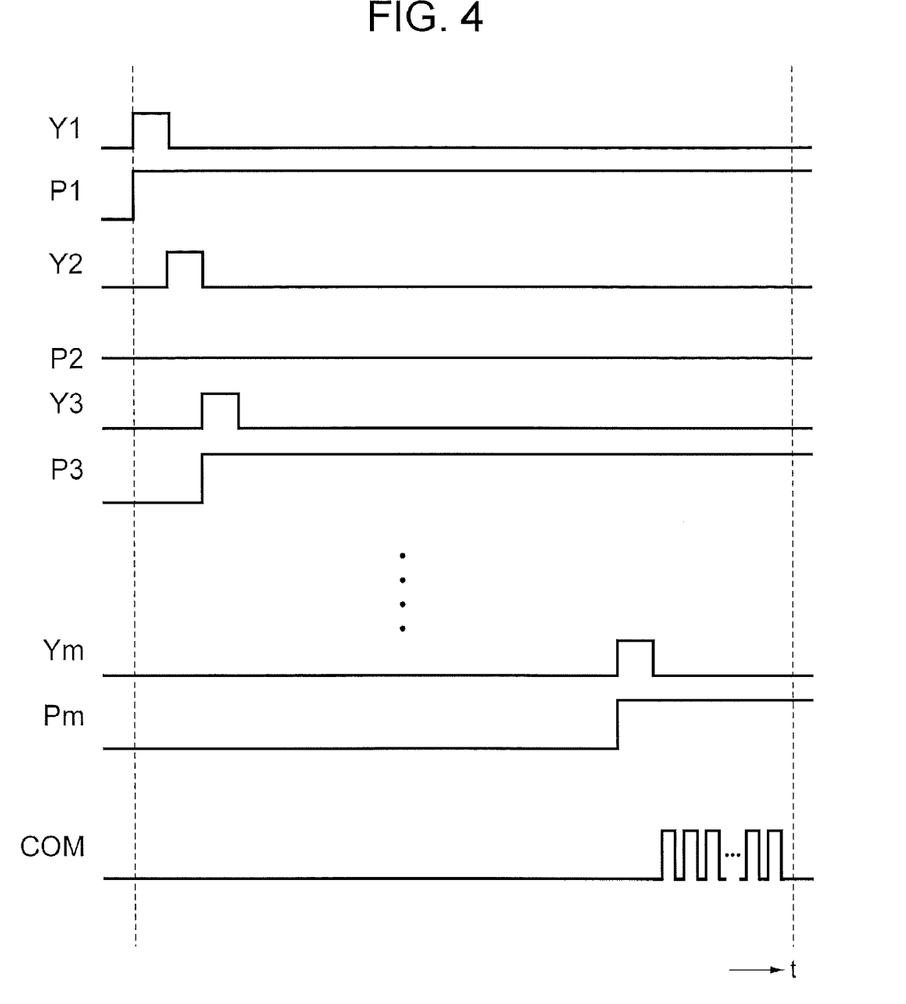
FIG. 4 is a timing chart explaining the operation of the electrophoretic device.

FIG. 4 is a timing chart explaining the operation of the electrophoretic device 100. Referring to FIG. 4, the scan signals Y1, Y2, ..., and Ym supplied to the gates of the respective transistors 103 via the scan lines 101, the potentials P1, P2, ..., and Pm of the first electrodes (individual electrodes) 105 in the respective electrophoretic elements 104, and the common electrode signal COM supplied to the second electrode (common electrode) 106 in the respective electrophoretic elements 104 are plotted against time t as abscissa. The timing chart of FIG. 4 corresponds to one write time. Although the potentials of the first electrodes 105 of the respective electrophoretic elements 104 corresponding to the pixels 109 in the first column are illustrated and those in the other columns are omitted, the same timing chart applies to the other columns.

The scan line drive circuit 130 sequentially selects the pixels 109 in the respective rows. Specifically, the scan line drive circuit 130 sets the potential of the scan signal Y1 to be supplied to the scan line 101 in the first row to a high level (for example, +3 V), as shown in FIG. 4. Consequently, the high potential is supplied to the gate of the transistor 103 included in each of the pixels 109 connected to the scan line 101 in the first row, thus turning on the transistor 103.

At that time, the data line drive circuit 140 sets the potential of each of the data signals D1, D2, ..., and Dn to be supplied to the respective data lines 102 to either the reference potential or a first potential (for example, +10 V) higher than the reference potential. Specifically, the data line drive circuit 140 supplies the first potential to each pixel 109 for black display and supplies the reference potential to each pixel 109 for white display in accordance with image data supplied from the controller 190. Consequently, either the reference potential or the first potential is applied to the first electrode 105 of the electrophoretic element 104 and one terminal of the capacitor 108 via the data line 102 through the transistor 103 in each of the pixels 109 in the selected first row. The applied potential is held by the capacitor 108 for a certain period of time (e.g., several hundreds of milliseconds to several seconds). In other words, the embodiment uses the capacitor 108 having an enough electrostatic capacitance to hold the potential (i.e., charge) for a period corresponding to one write time. As shown in FIG. 4, therefore, after the scan line 101 in the first row enters an unselected state, the potential applied to the first electrode 105 of the electrophoretic element 104 is held in each of the pixels 109 connected to the scan line 101 in the first row. At that time, the common electrode control circuit 150 applies the reference potential to the second electrode 106, serving as the common electrode. The potential of the second electrode 106 is held at the reference potential by the common electrode control circuit 150 while the scan line drive circuit 130 selects any scan line.

Similarly, the scan lines 101 in the second and subsequent rows and the pixels 109 connected to the respective scan lines 101 are controlled. Specifically, the scan line drive circuit 130 sequentially controls the scan lines 101 in the second and subsequent rows such that the potential of each of the scan signals Y2 to Ym becomes high (scan line selection control). The data line drive circuit 140 sets the potential of each of the data signals D1, D2, ..., and Dn to be supplied to the respective data lines 102 to either the reference potential or the first potential in accordance with image data. As described above, while the scan line drive circuit 130 selects any scan line, the common electrode control circuit 150 applies the reference potential to the second electrode 106, serving as the common electrode. Time required to select a single scan line 101 and write a voltage into the pixels 109 connected to the selected scan line is, for example, approximately several hundreds of microseconds. Time required to sequentially select all of the scan lines 101 is, for example, approximately several hundreds of milliseconds.

Following the above-described scan line selection control, the common electrode control circuit 150 supplies a signal, which fluctuates between a second potential equal to or higher than the reference potential and a third potential higher than the second potential, to the second electrode (common electrode) 106. In the embodiment, the second potential is equal to the reference potential and the third potential is equal to the first potential. Accordingly, the common electrode control circuit 150 supplies a single-polarity pulsed signal fluctuating between 0 V and +10 V to the second electrode 106 via the respective interconnection lines 201 (pulse driving), as shown in FIG. 4. This signal having a frequency of several tens of hertz (e.g., approximately 30 Hz) is applied for several seconds (e.g., 1 to 2 seconds). Those values are examples and may be appropriately changed. The relationship between the potential of each first electrode 105 and that of the second electrode 106 will now be described in detail below.

Figure 5:
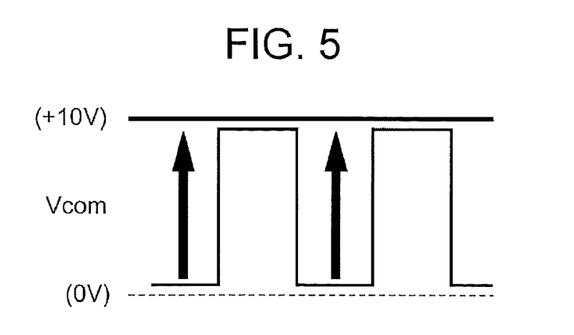
FIG. 5 is a waveform chart explaining the relationship between the potential of a first electrode and that of a second electrode.
Figure 6:
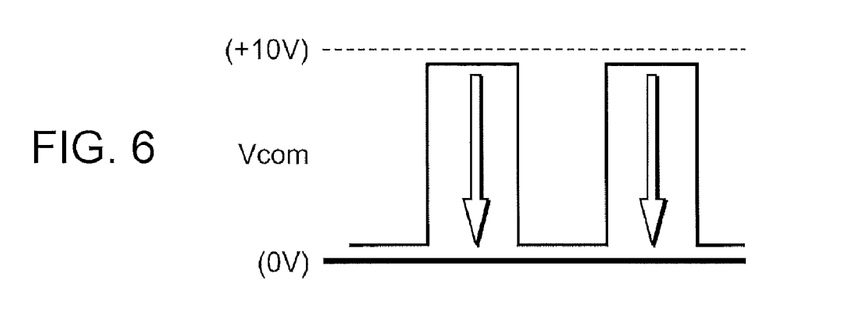
FIG. 6 is a waveform chart explaining the relationship between the potential of the first electrode and that of the second electrode.

FIGS. 5 and 6 are waveform charts explaining the relationship between the potentials of the first and second electrodes. As described above, the potential of each first electrode 105 is set to the first potential (e.g., +10 V) or the reference potential (e.g., 0 V). The potential of the second electrode 106 fluctuates between the second potential (e.g., 0 V) and the third potential (e.g., +10 V).

Regarding the pixel 109 in which the first potential (+10 V in this case) is written into the first electrode 105, when the potential of the second electrode 106 becomes the reference potential (0 V in this case) as shown in FIG. 5, a potential difference of +10 V (indicated by black upward arrows in FIG. 5) is created between the first electrode 105 and the second electrode 106. The periodic potential difference (electric field) causes the black particles (charged positively) contained in the electrophoretic layer 107 to be attracted to the second electrode 106 and causes the white particles (charged negatively) to be attracted to the first electrode 105. Therefore, in each pixel 109 which should display black color, an effect of enhancing (or additionally displaying) black color is obtained. When the potential of the second electrode 106 becomes the third potential, the potential difference between the first electrode 105 and the second electrode 106 becomes 0 V. Accordingly, a force that allows electrophoretic particles (black and white particles) to migrate is not caused.

As for the pixel 109 in which the reference potential (0 V in this case) is written into the first electrode 105, as shown in FIG. 6, when the potential of the second electrode 106 becomes the third potential (+10 V in this case), a potential difference of −10 V (indicated by white downward arrows in FIG. 6) is created between the first electrode 105 and the second electrode 106. The periodic potential difference (electric field) causes the black particles (charged positively) contained in the electrophoretic layer 107 to be attracted to the first electrode 105 and causes the white particles (charged negatively) to be attracted to the second electrode 106. Therefore, in each pixel 109 which should display white color, an effect of enhancing (or additionally displaying) white color is obtained. When the potential of the second electrode 106 becomes the reference potential, the potential difference between the first electrode 105 and the second electrode 106 becomes 0 V. Accordingly, a force that allows electrophoretic particles (black and white particles) to migrate is not produced.

A modification of the above-described embodiment (hereinafter, referred to as "first embodiment" for convenience) will now be described below.

Figure 7:
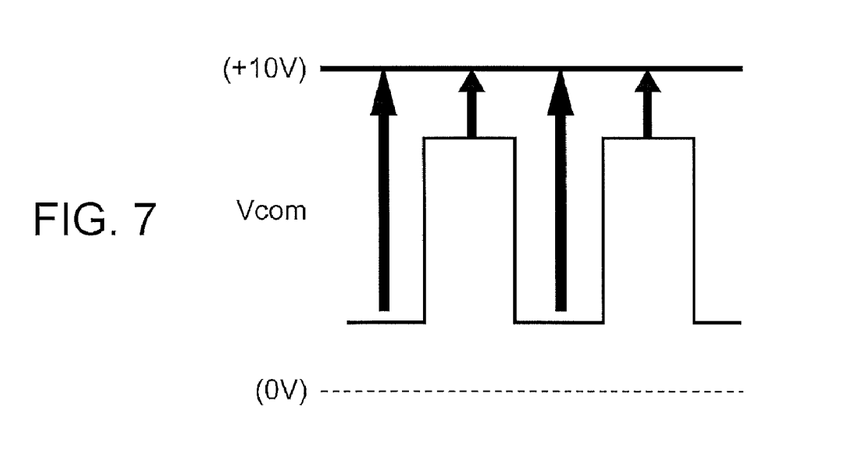
FIG. 7 is a waveform chart explaining the relationship between the potential of the first electrode and that of the second electrode.
Figure 8:
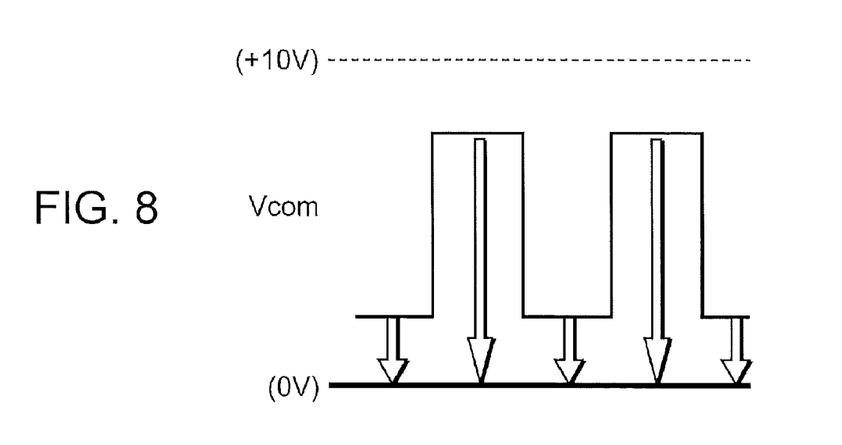
FIG. 8 is a waveform chart explaining the relationship between the potential of the first electrode and that of the second electrode.

FIGS. 7 and 8 are waveform charts explaining the relationship between the potentials of the first and second electrodes. The modification, which will be described below with reference to FIGS. 7 and 8, will be called a "second embodiment". As for potentials applied to the second electrode 106, the second potential may be higher than the above-described reference potential and the third potential may be lower than the above-described first potential, as shown in FIGS. 7 and 8. Specifically, the second potential is set to, for example, a value ranging from +2 to +3 V and the third potential is set to, for example, a value ranging from +7 to +8 V in the second embodiment. In other words, according to the second embodiment, the second electrode is supplied with a signal that fluctuates between the second potential higher than the reference potential (0 V in this case) and the third potential lower than the first potential (+10 V in this case). At that time, each first electrode 105 is at the first potential (e.g., +10 V) or the reference potential (e.g., 0 V).

Regarding the pixel 109 in which the first potential (+10 V in this case) is written into the first electrode 105, as shown in FIG. 7, when the potential of the second electrode 106 becomes the second potential (ranging from +2 to +3 V in this case), a potential difference of +7 to +8 V (indicated by black long upward arrows in FIG. 7) is created between the first electrode 105 and the second electrode 106. When the potential of the second electrode 106 becomes the third potential (ranging from +7 to +8 V in this case), a potential difference of +2 to +3 V is established between the first electrode 105 and the second electrode 106. Those potential differences (electric fields) cause the black particles (charged positively) contained in the electrophoretic layer 107 to be attracted to the second electrode 106 and cause the white particles (charged negatively) to be attracted to the first electrode 105. Therefore, in each pixel 109 which should display black color, the effect of enhancing (or additionally displaying) black color is obtained.

As for the pixel 109 in which the reference potential (+0 V in this case) is written into the first electrode 105, as shown in FIG. 8, when the potential of the second electrode 106 becomes the second potential (ranging from +2 to +3 V in this case), a potential difference of −2 to −3 V (indicated by white long downward arrows in FIG. 8) is generated between the first electrode 105 and the second electrode 106. When the potential of the second electrode 106 becomes the third potential (ranging from +7 to +8 V in this case), a potential difference of −7 to −8 V is established between the first electrode 105 and the second electrode 106. Those potential differences (electric fields) cause the white particles (charged negatively) contained in the electrophoretic layer 107 to be attracted to the second electrode 106 and cause the black particles (charged positively) to be attracted to the first electrode 105. Therefore, in each pixel 109 which should display white color, the effect of enhancing (or additionally displaying) white color is obtained.

In the second embodiment described with reference to FIGS. 7 and 8, although the potential difference varies every half period of the signal supplied to the second electrode 106, the potential differences are established between the first electrode 105 and the second electrode 106 for the whole period. Consequently, the electrophoretic particles are enabled to migrate (move) more efficiently. Particularly, the second embodiment is effective in a case where a so-called kickback (turning back) phenomenon remarkably occurs. The term "kickback" means the following phenomenon: An electric field is applied to move electrophoretic particles. After that, when the electric field is set to zero, the electrophoretic particles turn back. The detailed causes are not yet clear.

Figure 9:
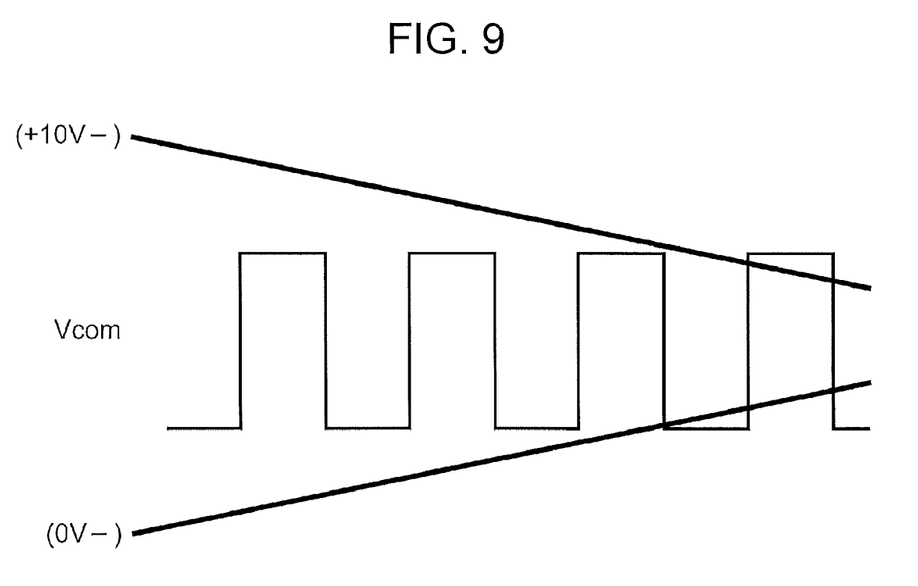
FIG. 9 is a diagram explaining further advantages of a second embodiment.

FIG. 9 is a diagram explaining further advantages of the second embodiment. The above description has been made assuming that the potential of the first electrode 105 is a constant value. Actually, the potential of the first electrode 105 may vary as shown in FIG. 9. Specifically, if the first potential (e.g., +10 V) is applied to the first electrode 105, the potential of the first electrode 105 may fall over time. This fall is caused by leak current to the second electrode 106 or off-state current of the transistor 103. Similarly, if the reference potential (e.g., 0 V) is applied to the first electrode 105, the potential of the first electrode 105 may rise over time. This rise is caused by leak current to the second electrode 106. A change in potential of the first electrode 105 remarkably occurs in a case where the hold capacitance of the capacitor 108 is not sufficiently large. At that time, if the potential of the first electrode 105 in the pixel 109 to be controlled to display black color is lower than the potential of the second electrode 106, the pixel is not controlled to display black color. Disadvantageously, the pixel displays another color close to white. Similarly, if the potential of the first electrode 105 in the pixels 109 to be controlled to display white color is higher than the potential of the second electrode 106, the pixel is not controlled to display white color. Disadvantageously, the pixel displays another color close to black. To prevent those disadvantages of the second embodiment in which the hold capacitance of the capacitor 108 is not sufficiently large, preferably, the second potential to be applied to the second electrode 106 is higher than the reference potential and the third potential to be applied to the second electrode 106 is lower than the first potential. Setting the second and third potentials in consideration of a decrease in potential of the first electrode 105 caused by leak current can prevent display color inversion (i.e., inversion of a dispersion state of electrophoretic particles). In another respect, the use of the above-described setting can further reduce the hold capacitance of the capacitor 108. Advantageously, this results in a reduction in the layout area of the capacitor 108, simplification of the manufacturing process, and improvement of the aperture ratio of the pixel.

Figure 10:
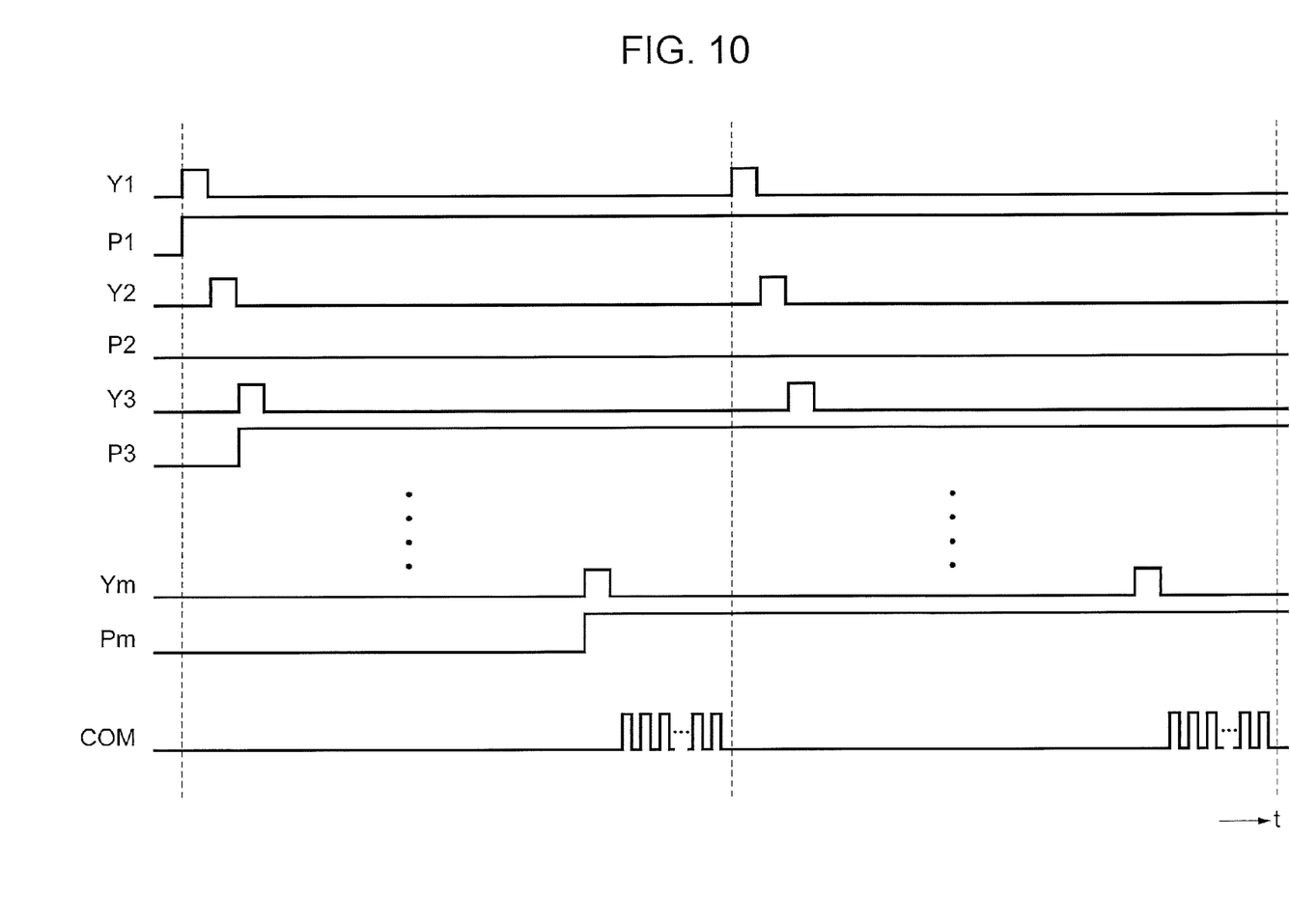
FIG. 10 is a diagram explaining a third embodiment.

FIG. 10 is a diagram explaining a third embodiment. In the above-described first and second embodiments, if the electrostatic capacitance of the capacitor 108 is not sufficiently large or a leak current is large, disadvantageously, display quality may be deteriorated, for example, the contrast may be lowered or image lag may occur. To solve the above-described problems, preferably, the above-described voltage writing control and pulse driving control using a single-polarity pulsed signal are repeated a plurality of times, as shown in FIG. 10. FIG. 10 shows a case where the respective controls are repeated two times. The controls may be repeated three or more times. Consequently, the deterioration of image quality can be prevented.

Examples of electronic apparatuses each including the above-described electrophoretic device as a display unit will now be described below.

Figure 11A:
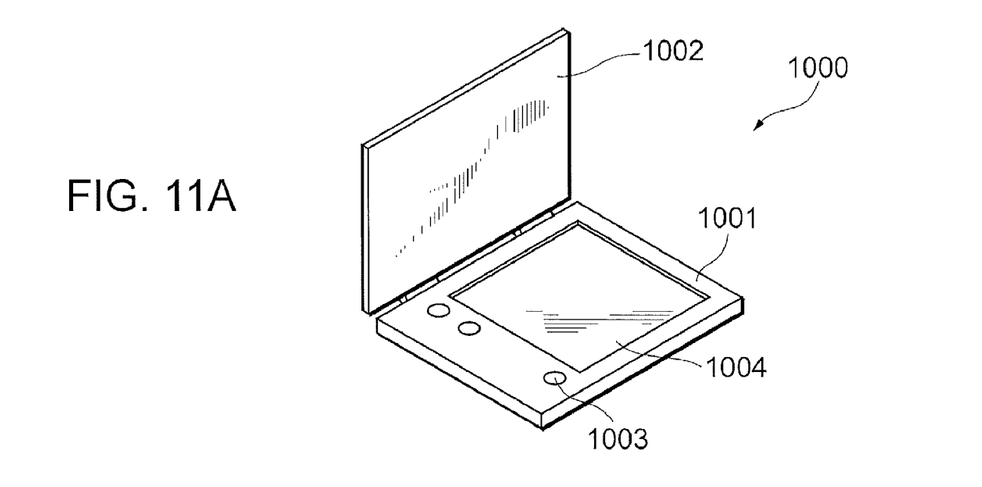
FIGS. 11A to 11C are perspective views explaining concrete examples of electronic apparatuses each including the electrophoretic device.
Figure 11B:
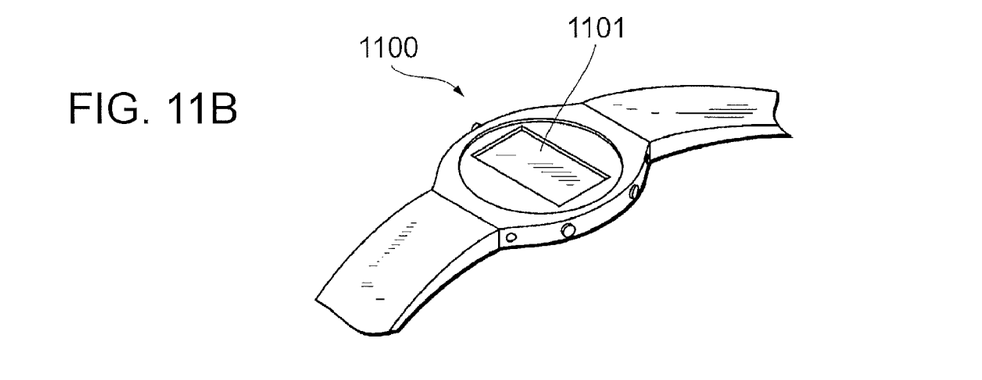
Figure 11C:
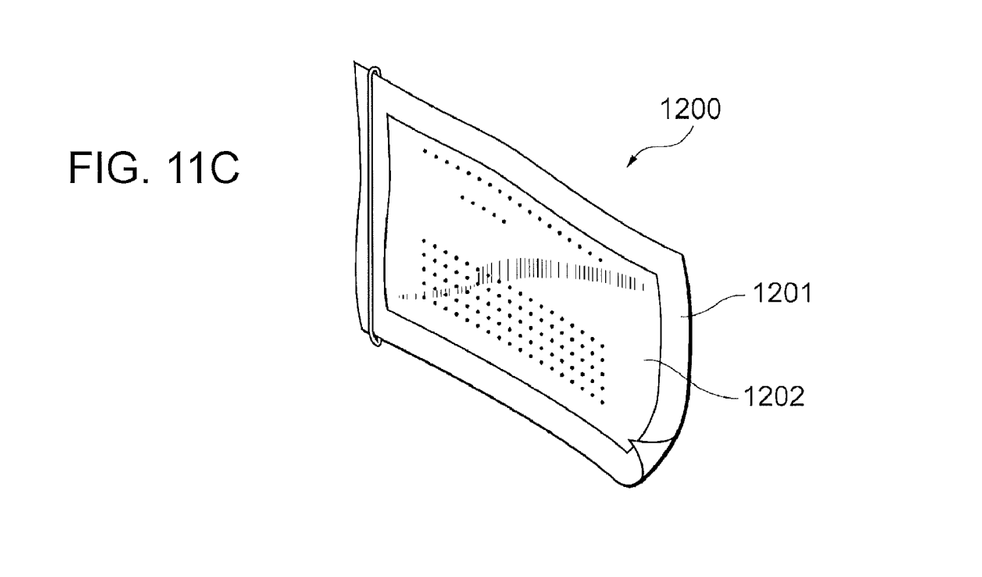

FIGS. 11A to 11C are perspective views of electronic apparatuses each of which the electrophoretic device according to any of the embodiments of the invention is applied to. FIG. 11A is a perspective view of an electronic book as one example of the electronic apparatuses. The electronic book 1000 includes a book-shaped frame 1001, an openable cover 1002 pivotally attached to the frame 1001, an operation unit 1003, and a display unit 1004 that includes the electrophoretic device according to any of the embodiments. FIG. 11B is a perspective view of a watch as one example of the electronic apparatuses. The watch 1100 includes a display unit 1101 that includes the electrophoretic device according to any of the embodiments. FIG. 11C is a perspective view of an electronic paper as one example of the electronic apparatuses. The electronic paper 1200 includes a main body 1201 and a display unit 1202 that includes the electrophoretic device according to any of the embodiments. The main body 1201 includes a rewritable sheet having a texture like paper and flexibility. Electronic apparatuses to which the electrophoretic device can be applied are not limited to the above-described examples but widely include apparatuses using a change in color tone of visual sense caused by migration of charged particles.

As described above, according to the embodiments, a voltages is written into the pixel while the first potential is applied to the first electrode of the photoelectric element and the reference potential is applied to the second electrode thereof (first state), alternatively, while the reference potential is applied to each of the first and second electrodes. Accordingly, the states of the electrophoretic elements can be rewritten more rapidly than the case where the erase operation is performed before the voltage write operation. Since the potential written in the first electrode is held by the capacitor for a certain period, the next control can be performed for this period. In other words, the potential applied to the second electrode is allowed to fluctuate between the second potential and the third potential. Consequently, for example, in the above-described first state, the potential of the first electrode is periodically made higher than that of the second electrode, thus accelerating migration of the electrophoretic particles. Similarly, in the above-described second state, the potential of the second electrode is periodically made higher than that of the first electrode, thus accelerating migration of the electrophoretic particles. Advantageously, in each of the first and second states, if the preceding voltage write operation is insufficiently performed, the effect of complementing the insufficient operation can be obtained. In other words, according to the electrophoretic device of any of the embodiments and a method of driving the electrophoretic device, the electrophoretic particles in each electrophoretic element can be more reliably dispersed irrespective of a voltage write state (the first or second state) by application of a signal fluctuating after the state.

The invention is not limited to the above-described embodiments but many modifications and variations may be made within the scope of the invention. For example, the above-described embodiments have been described with respect to the case where the invention is applied to the electrophoretic device having a plurality of pixels arranged in a matrix. The arrangement of the pixels is not limited to this example. Similarly, the range of applications of the invention is not limited to electrophoretic display devices. Although a drive signal having a rectangular waveform has been described as an example of a signal for pulse driving, another alternating current signal in sine wave form may be used.

What is claimed is:

1. A method of driving an electrophoretic device having a plurality of scan lines, a data line crossing the plurality of scan lines, a plurality of pixels each corresponding to an intersection between one of the plurality of scan lines and the data line, each of the plurality of pixels including a first electrode, a second electrode, and an electrophoretic layer disposed between the first and second electrodes, each pixel further including a capacitor connected to the first electrode at one terminal, the plurality of pixels including a first pixel and a second pixel, the method comprising:

sequentially selecting the plurality of scan lines, applying a reference potential via the data line to the first electrode and the terminal of the capacitor in the first pixel which is connected to the selected scan line, applying the reference potential to the second electrode of the first pixel, applying a first potential higher than the reference potential via the data line to the first electrode and the terminal of the capacitor in the second pixel which is connected to the selected scan line, and applying the reference potential to the second electrode of the second pixel; and during a first period of time, applying a signal to the second electrode after completion of the sequentially selecting, wherein the signal alternates between a second potential and a third potential a plurality of times during the first period of time, the second potential being higher than the reference potential, the third potential being higher than the second potential and being lower than the first potential, wherein during the first period of time, the electric potential of the first electrode of the second pixel decreases from the first potential but remains above a fourth potential, wherein the third potential is lower than the fourth potential, and wherein an electric potential of the second electrode does not change during selecting the plurality of scan lines.

2. The method according to claim 1, wherein the sequentially selecting and the applying the signal are repeated more than one time.

3. The method according to claim 1, wherein during sequentially selecting the plurality of scan lines, the reference potential is applied to the first electrode and the terminal of the capacitor in a first pixel, and the first potential is applied to the first electrode and the terminal of the capacitor in a second pixel.

4. The method according to claim 1,
wherein during the first period of time, the electric potential of the first electrode of the first pixel increases from the reference potential to a fifth potential, and
wherein the second potential is higher than the fifth potential.

5. An electrophoretic device comprising:
a plurality of scan lines;
a data line crossing the plurality of scan lines;
a plurality of pixels each corresponding to an intersection between one of the plurality of scan lines and the data line, the plurality of pixels including a first pixel and a second pixel; and
a drive circuit connected to the pixels, wherein
each pixel includes a first electrode, a second electrode, an electrophoretic layer disposed between the first and second electrodes, and a capacitor connected to the first electrode at one terminal, and
the drive circuit performs:
sequentially selecting the plurality of scan lines, applying a reference potential via the data line to the first electrode and the terminal of the capacitor in the first pixel which is connected to the selected scan line, and applying the reference potential to the second electrode of the first pixel, applying a first potential higher than the reference potential via the data line to the first electrode and the terminal of the capacitor in the second pixel which is connected to the selected scan line, and applying the reference potential to the second electrode of the second pixel; and during a first period of time, applying a signal to the second electrode after completion of the sequentially selecting, wherein the signal alternates between a second potential and a third potential a plurality of times during the first period of time, the second potential being higher than the reference potential, the third potential being higher than the second potential and being lower than the first potential, wherein during the first period of time, the electric potential of the first electrode of the second pixel decreases from the first potential but remains above a fourth potential, wherein the third potential is lower than the fourth potential, and wherein an electric potential of the second electrode does not change during selecting the plurality of scan lines.

6. The electrophoretic device according to claim 5, wherein the second electrode is a common electrode shared by the pixels.

7. The electrophoretic device according to claim 5, wherein the drive circuit repeats the sequentially selecting and the applying the signal more than one time.

8. An electronic apparatus comprising the electrophoretic device according to claim 5 as a display unit.

9. The electrophoretic device according to claim 5, wherein during sequentially selecting the plurality of scan lines, the reference potential is applied to the first electrode and the terminal of the capacitor in a first pixel, and the first potential is applied to the first electrode and the terminal of the capacitor in a second pixel.

10. The electrophoretic device according to claim 5, wherein during the first period of time, the electric potential of the first electrode of the first pixel increases from the reference potential to a fifth potential, and wherein the second potential is higher than the fifth potential.

* * * * *